US007090993B2

(12) United States Patent
Brady et al.

(10) Patent No.: US 7,090,993 B2
(45) Date of Patent: Aug. 15, 2006

(54) METHOD OF ASSAYING PYRROLE-CONTAINING BIOLOGICAL COMPOUNDS

(75) Inventors: Jeffrey D. Brady, Broughty Ferry (GB); Simon P. Robins, Inverurie (GB)

(73) Assignee: Rowett Research Institute, Aberdeen (GB)

( * ) Notice: Subject to any disclaimer, the term of this patent is extended or adjusted under 35 U.S.C. 154(b) by 61 days.

(21) Appl. No.: 10/672,843

(22) Filed: Sep. 26, 2003

(65) Prior Publication Data
US 2004/0063222 A1   Apr. 1, 2004

Related U.S. Application Data

(60) Division of application No. 09/970,328, filed on Oct. 3, 2001, now Pat. No. 6,667,180, which is a continuation-in-part of application No. 09/679,141, filed on Oct. 3, 2000, now abandoned.

(51) Int. Cl.
  G01N 33/53    (2006.01)
  G01N 33/532   (2006.01)
  G01N 33/552   (2006.01)
  C07K 17/14    (2006.01)

(52) U.S. Cl. .................. 435/7.5; 435/7.1; 436/527; 436/544; 436/531; 436/532; 436/96; 436/815; 530/405; 548/303.7

(58) Field of Classification Search ............... 530/403, 530/405; 548/303.7; 436/96, 527, 531, 436/532, 544, 545, 546, 815; 435/7.5, 7.1
See application file for complete search history.

(56) References Cited

U.S. PATENT DOCUMENTS

| | | | |
|---|---|---|---|
| 4,628,027 A | 12/1986 | Gay | 435/7 |
| 4,973,666 A | 11/1990 | Eyre | 530/323 |
| 5,140,103 A | 8/1992 | Eyre | 530/327 |
| 5,300,434 A | 4/1994 | Eyre | 435/240.2 |
| 5,320,970 A | 6/1994 | Eyre | 436/536 |
| 5,455,179 A | 10/1995 | Eyre | 436/536 |
| 5,472,884 A | 12/1995 | Eyre | 436/518 |
| 5,473,052 A | 12/1995 | Eyre | 530/387.9 |
| 5,532,169 A | 7/1996 | Eyre | 436/518 |
| 5,576,189 A | 11/1996 | Eyre | 435/7.93 |
| 5,607,862 A | 3/1997 | Eyre | 436/501 |
| 5,641,687 A | 6/1997 | Eyre | 436/518 |
| 5,641,837 A | 6/1997 | Eyre | 435/7.1 |
| 5,652,112 A | 7/1997 | Eyre | 435/7.1 |
| 5,656,439 A | 8/1997 | Eyre | 435/7.1 |
| 5,677,198 A | 10/1997 | Eyre | 436/518 |
| 5,688,652 A | 11/1997 | Eyre | 435/7.1 |
| 5,700,693 A | 12/1997 | Robins | 436/64 |
| 5,700,694 A | 12/1997 | Robins | 436/64 |
| 5,702,909 A | 12/1997 | Eyre | 435/7.9 |
| 5,736,344 A | 4/1998 | Kung | 435/7.9 |
| 5,750,647 A | 5/1998 | Eyre | 530/328 |
| 5,817,755 A | 10/1998 | Eyre | 530/328 |
| 5,834,221 A | 11/1998 | Eyre | 435/7.92 |
| 5,912,131 A | 6/1999 | Eyre | 435/7.1 |
| 5,919,634 A | 7/1999 | Eyre | 435/7.1 |
| 5,939,274 A | 8/1999 | Eyre | 435/7.1 |
| 5,945,274 A | 8/1999 | Eyre | 435/4 |
| 5,962,236 A | 10/1999 | Eyre | 435/7.1 |
| 5,962,639 A | 10/1999 | Eyre | 530/329 |
| 5,972,623 A | 10/1999 | Krane | 435/7.1 |
| 6,010,863 A | 1/2000 | Te Koppele | 435/7.1 |
| 6,025,144 A | 2/2000 | Eyre | 435/7.1 |
| 6,027,903 A | 2/2000 | Eyre | 435/7.1 |

FOREIGN PATENT DOCUMENTS

WO     WO86/06374     11/1986

OTHER PUBLICATIONS

Adamczyk, et al.: "Synthesis of Immunoreagents for Detection of Deoxypyrrololine, a Cross-link of Bone Collagen", *Bioorganic & Medicinal Chemistry Letters*, vol. 10, pp. 269-271 (2000).

Atley, et al.: "Proteolysis of Human Bone Collagen by Cathepsin K: Characterization of the Clevage Sites Generating the Cross-Linked N-Telopeptide Neopitope", *Bone*, vol. 26, No. 3, pp. 241-247, Mar. 2000.

Brame, et al: Identification of Extremely Reactive γ-Ketoaldehydes (Isolevuglandins) as Products of the Isoprostane Pathway and Characterization of Their Lysyl Protein Adducts, *The Journal of Biological Chemistry*, vol. 274, No. 19, pp. 13139-13146, May 7, 1999.

Hanson, et al: "Molecular Site Specificity of Pyridinoline and Pyrrole Cross-links in Type 1 Collagen of Human Bone", *The Journal of Biological Chemistry*, vol. 271, No. 43, pp. 26508-26516, Oct. 25, 1996.

Hughes, et al: "A Collagen-associated Ehrlich Chromogen: a Pyrrolic Cross-link?", *Bioscience Reports* (UK), vol. 1, pp. 611-618, (1981).

(Continued)

*Primary Examiner*—Mary E. Ceperley
*Assistant Examiner*—Shafiqul Haq
(74) *Attorney, Agent, or Firm*—Crowell & Moring LLP

(57) ABSTRACT

This invention relates to a method of assaying pyrrole-containing biological compounds and chemical compositions that can be used in the method. The method involves contacting a biological compound with one of:
a) a bound or bindable derivatizing agent which forms a reaction product with the biological compound, followed by exposure to a detectable molecule which forms a complex with the reaction product; or
b) a derivatizing agent which forms a reaction product with the biological compound, followed by exposure to a bound binding agent specific to the biological compound in the reaction product; or
c) a binding agent specific to the biological compound, followed by exposure to a derivatizing agent which forms a reaction product with the biological compound, and determining the amount of bound biological compound. There is also provided a method of preparing an antigen.

33 Claims, 10 Drawing Sheets

OTHER PUBLICATIONS

Kemp, et al: "Ehrlich Chromogens, Probable Cross-links in Elastin and Collagen", *Biochemical Journal* (UK), vol. 252, pp. 387-393 (1988).

Kuypers, et al: "Identification of the Loci of the Collagen-associated Ehrlich Chromogen in Type 1 Collagen Confirms its Role as a Trivalent Cross-link", *Biochemical Journal* (UK), vol. 283, pp. 129-136 (1992).

Lombard, et al: "Comparison of Three Reagents for Detecting Indole Production by Anaerobic Bacteria in Microtest Systems", *Journal of Clinical Microbiology*, vol. 18, No. 3, pp. 609-613, Sep. 1983.

McBrayer, et al: "Diffusion of Metals in Silicon Dioxide", *Journal of Electrochemical Soceity*, vol. 133, No. 6, pp. 1242-1246, Jun. 1986.

Raghavan, et al: "Diffusion of Copper Through Dielectric Films Under Bias Temperature Stress", *Thin Solid Films*, vol. 262, pp. 168-176 (1995).

Rajkumar, et al: "Generation of Pyrroles in the Reaction of Levuglandin $E_2$ with Proteins", *Journal of Organic Chemistry*, vol. 59, pp. 6038-6043, (1994).

Ramanakoppa H. Nagaraj, et al: "Protein Modification by the Degradation Products of Ascorbate: Formation of a Novel Pyrrole from the Maillard Reaction of L-threose with Proteins", *Biochimica et Biophysica Acta*, vol. 1253, pp. 75-84 (1995).

Salomon, et al: "Protein Adducts of Iso[4]levuglandin $E_2$, a Product of the Isoprostane Pathway, in Oxidized Low Density Lippoprotein", *The Journal of Biological Chemistry*, vol. 274, No. 29, pp. 20271-20280, Jul. 16, 1999.

Scott, et al: "An Affinity Method for Preparing Polypeptides Enriched in the Collagen-Associated Ehrlich Chromogen", *Journal of Biochemistry*, vol. 93, pp. 921-925 (1983).

Chemical Abstracts 130:53792 abstracting German patent application 19723779 (1997).

Chemical Abstracts 127:122001 abstracting PCT Publication No. WO 9721685 (1997).

Chemical Abstracts 126:343579 abstracting PCT Publication No. WO 9714685 (1997).

Chemical Abstracts 128:47979 abstracting Japanese Publication No. 09301939 (1997).

Chemical Abstracts 125:86316 abstracting PCT Publication No. WO 9608483 (1996).

Chemical Abstracts 125:181171 abstracting European Patent No. 718710 (1996).

Chemical Abstracts 125:181170 abstracting European Patent No. 718709 (1996).

Chemical Abstracts 125:154318 abstracting European Patent No. 718708 (1996).

Chemical Abstracts 124:261609 abstracting European Publication No. 689845 (1996).

Chemical Abstracts 121:10000 abstracting German Publication No. 4232505 (1994).

Chemical Abstracts 120:271175 abstracting PCT Publication No. 9315047 (1993).

Chemical Abstracts 83:44737 abstracting German Publication No. 2435888 (1975).

G.K. Reddy and C.S. Enwemeka: "Methdo for Assaying Pyrrole-Containing biological Compounds", *Clinical biochemistry* 29(3): 225-229 (1996).

M. Stefak, A. Gajdosik, a. Gajdosikova, L. Krizanova, "Dimethylaminobenzaldehyde-reative substances in tail tendon collagen of streptozotocin-diabetic rats: temporal relation to biomechanical properties and advanced glycation endproduct (AGE)-related fluorescence", *Biochimica et Biophysical Acta* 1502:398-404 (2000).

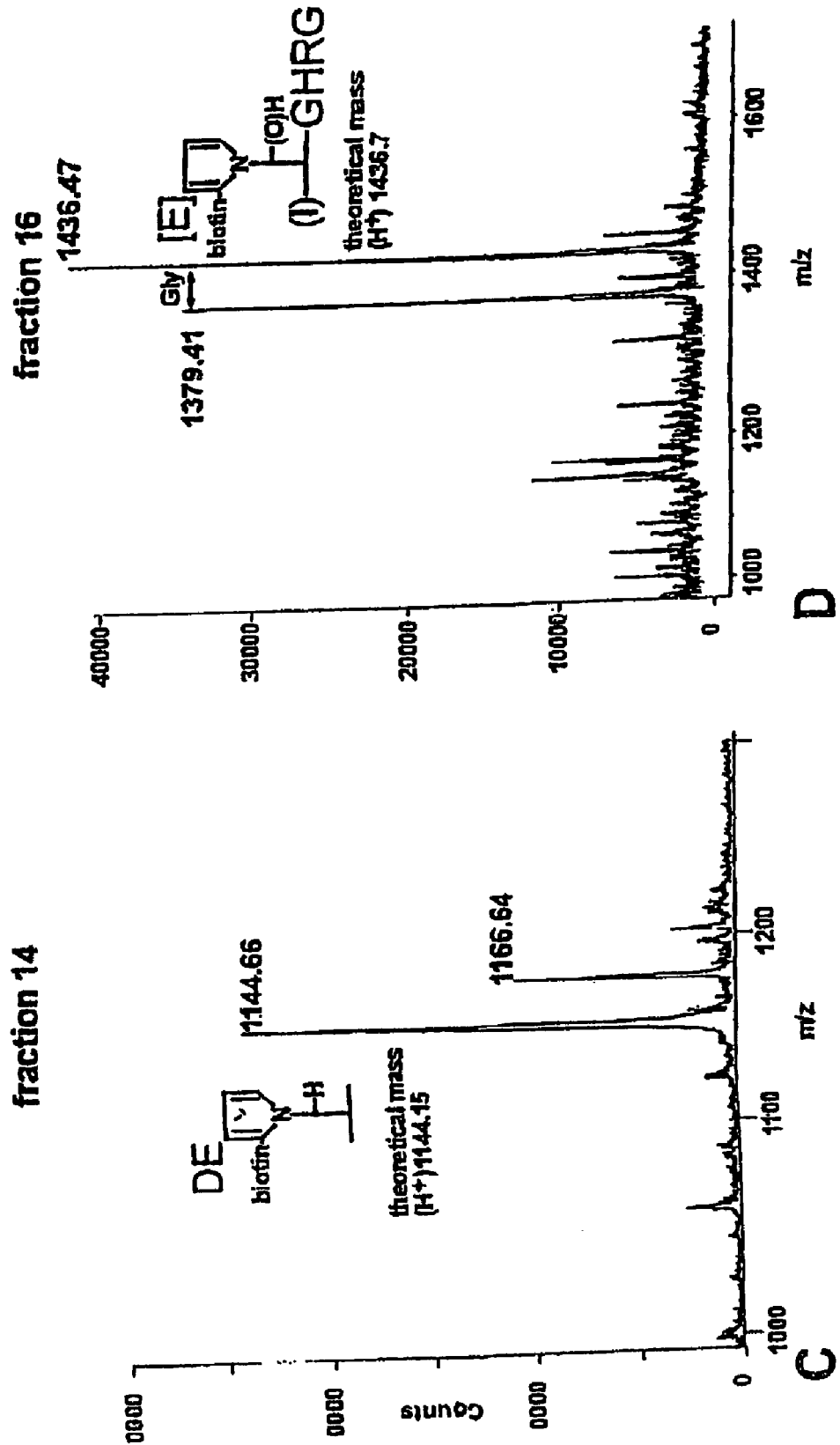
Fig. 1 con'd

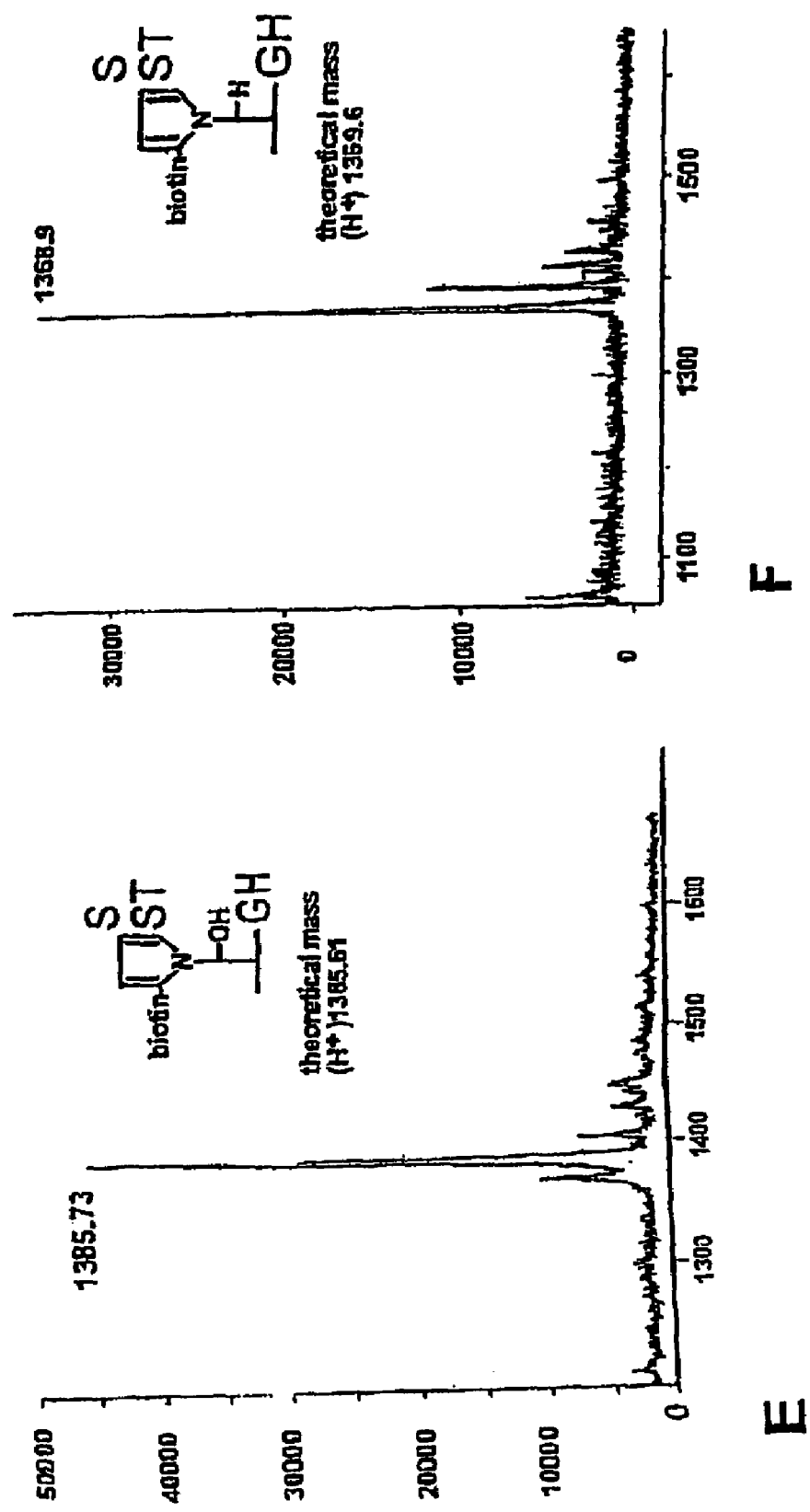
Fig.1 con'd

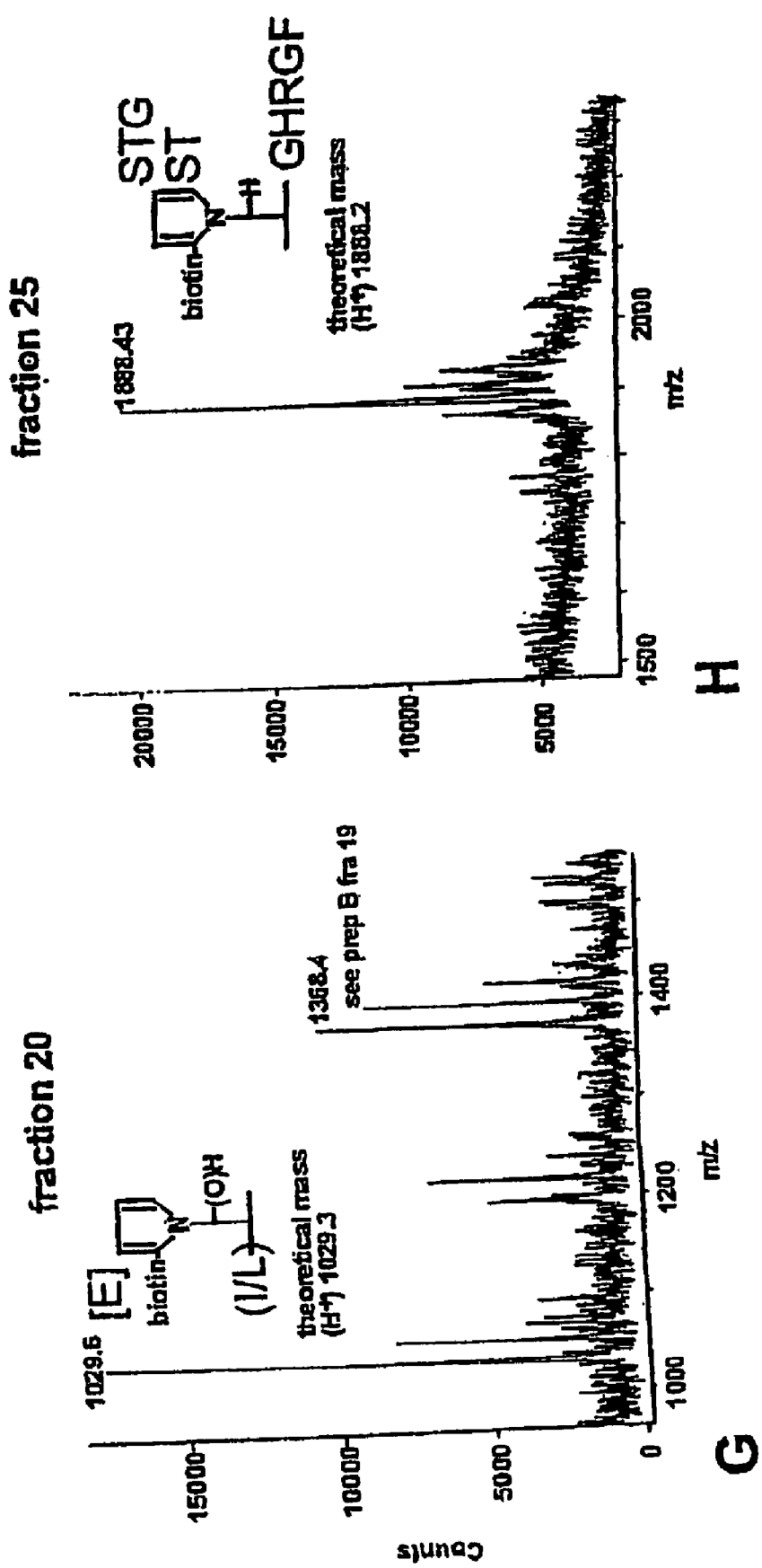
Fig. 1 con'd

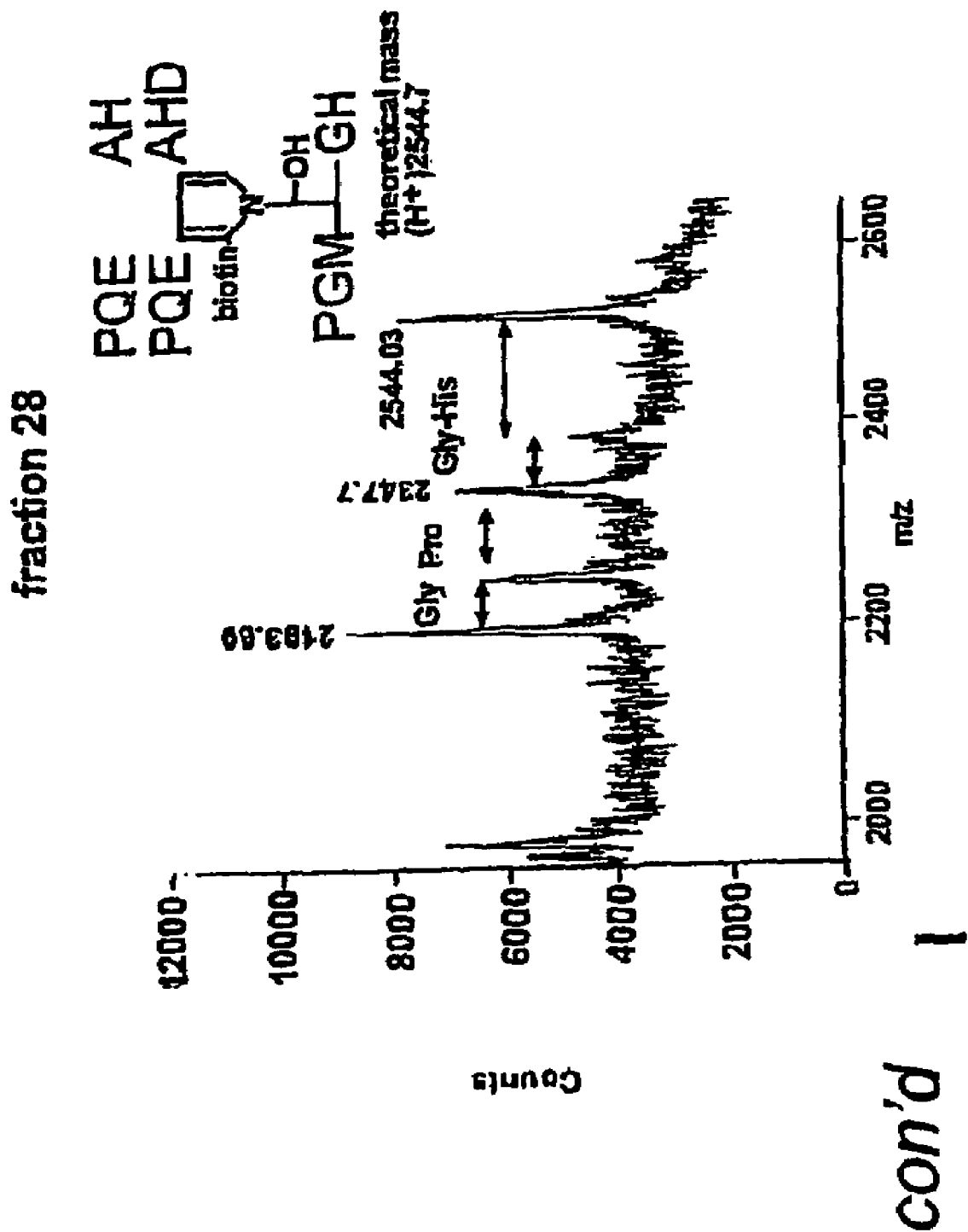
Fig. 1 con'd

METHOD OF ASSAYING PYRROLE-CONTAINING BIOLOGICAL COMPOUNDS

CROSS-REFERENCE TO RELATED APPLICATION

This application is a divisional of U.S. application Ser. No. 09/970,328, filed Oct. 3, 2001, now U.S. Pat. No. 6,667,180 which is a continuation-in-part of U.S. application Ser. No. 09/679,141, filed Oct. 3, 2000 (now abandoned), the disclosures of which are incorporated herein by reference.

BACKGROUND OF THE INVENTION

1. Field of the Invention

This invention relates to methods of assaying pyrrole-containing biological compounds and chemical compositions that can be used in such methods. More specifically, it relates to a method for detecting pyrrole-containing molecules that are markets of particular disease states.

2. Description of Related Art

Erlich's reagent, or p-dimethylaminobenzaldehyde (1), is a molecule that can react with pyrroles and indoles to form a chromogenic compound.

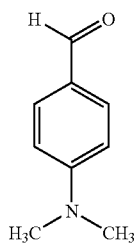

See G. Lombard and V. Dowell, *J. Clin. Microbiol.*

Scheme A

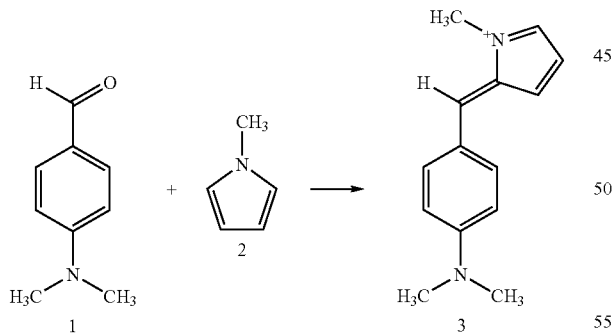

(1983) 18:609–613. The mechanism of action is typically described as an electrophilic attack on the α-carbon atom of a pyrrole. This attack forms a highly conjugated cation that absorbs light in the visible spectrum. Such a mechanism is graphically represented in Scheme A above.

The reaction of Ehrlich's reagent with certain compounds has been discussed. For instance, Iyer reported a pyrrole is formed when $LGE_2$ is reacted with proteins. See Iyer et al., *J. Org. Chem.* (1994) 59:6038–6043. When the pyrrole was contacted with Ehrlich's reagent in the presence of $BF_3.OEt_2$, a blue-green chromophore was produced. The chromophore was identified as a pyrrolic electrophilic substitution product.

Lombard reported the reaction between Ehrlich's reagent and bacterially derived indoles. See G. Lombard and V. Dowell, *J. Clin. Microbiol.* (1983) 18:609–613. The sensitivity of the reagent was compared to two other indole detecting compounds: Kovac's reagent and DMCA. Ehrlich's reagent was reported to be 10 times less sensitive than DMCA and 10 times more sensitive than Kovac's reagent in detecting indole.

While Ehrlich's reagent has been used to roughly detect the presence of pyrroles or indoles in a targeted material, improved compositions and methods for detecting such heterocycles are desirable, especially methods that provide for detecting pyrrole-containing molecules that are markers of particular disease states.

SUMMARY OF THE INVENTION

The present invention provides methods of assaying pyrrole-containing biological compounds.

In one case the method involves:
1) contacting the biological compound with either:
   a) an optionally labelled derivatizing agent (bound to or able to bind to a solid support), wherein the derivatizing agent forms a reaction product with the biological compound (preferably via covalent attachment thereto), followed by exposure to a detectable molecule which forms a complex with the reaction product; or
   b) an optionally labelled derivatizing agent not bound to a solid support, wherein the derivatizing agent forms a reaction product with the biological compound (preferably via covalent attachment thereto), followed by exposure to a binding agent specific to the biological compound in the reaction product, said binding agent being bound to a solid support; or
   c) a binding agent bound to a solid support, said binding agent being specific to the biological compound and forming a complex therewith, followed by exposure to an optionally labelled, derivatizing agent which forms a reaction product with the biological compound moiety of said complex (preferably via covalent attachment thereto); and
2) determining the amount of bound biological compound by detecting the detectable molecule, or by determining the amount of free or bond binding agent or by measuring the amount of label present.

Preferably, the method of assaying pyrrole-containing biological compounds is Method 1, described in part a) above. Method 1 involves the following steps:
1) contacting a biological compound with a derivatizing agent of the following structure in the bound form;

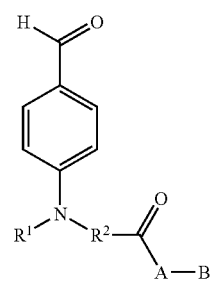

wherein $R^1$ is an alkyl group, $R^2$ is an alkyl group, A is a linking group and B is a solid support, and wherein the contact induces formation of a reaction product, and wherein the reaction product comprises the covalent attachment of the biological compound to the derivatizing agent; followed by contacting the reaction product with a detectable molecule, wherein the contact induces specific binding of the detectable molecule to the reaction product to provide a complex; and 2) determining the amount of bound biological material by detecting the detectable molecule.

Preferably the detectable molecule is a monoclonal antibody (MAb) specific to the biological compound. Preferably the solid support is a microtitre or a treated glass slide.

Preferably the method of assaying pyrrole-containing biological compounds is Method 2 described in part b) above. Method 2 involves the following steps:

1) contacting the biological compound with an optionally labelled derivatizing agent in solution to form a reaction product therewith (preferably via covalent attachment thereto) followed by exposure to a binding agent bound to a solid support, said binding agent being specific to the biological compound in the reaction product and 2) determining the amount of bound biological compound by determining the amount of labelled derivatizing agent bound to the solid support.

Preferably the derivatizing agent is biotinylated Ehrlich's reagent. Preferably the solution containing the reaction product is neutralised prior to contact with the bound binding agent. Preferably the bound MAb is bound to a solid support, suitably a microtitre plate or a treated glass slide.

Preferably the derivatizing agent is labelled with a labeling molecule, suitably a radio-labelled, fluorescent label, enzyme label or the like. Preferably the amount of bound biological compound is determined by detecting the amount of labelled derivatizing agent bound on the solid support.

Method 2 takes into account the fact that relatively strong acid conditions are required for the reaction of derivatizing reagents with pyrroles. Thus, most non-covalent interactions, such as antibody-antigen complexes, would be disrupted under these conditions. To overcome this problem, pyrrolic units in the biological sample are targeted in Method 2 by reaction in solution with derivatizing agent to form a reaction product, preferably via covalent attachment thereto followed by capture of the reaction product on a surface coated with specific antibodies.

Preferably, the method of assaying pyrrole-containing biological compounds is Method 3, described in part a) above. Method 3 involves the following steps:

1) contacting a biological compound with a derivatizing agent in solution to form a reaction product wherein the derivatizing agent comprises a first partner of a strong binding pair.

2) contacting the reaction product with a solid support having a second partner of the strong binding pair on its surface, to form a bound complex with the reaction product;

3) contacting the bound complex with a detectable molecule;

4) determining the amount of bound biological compound by detecting the amount of detectable molecule bound to the solid support.

Preferably the derivatizing agent is a p-dimethylaminobenzaldehyde derivative, and in bound form has the following structure:

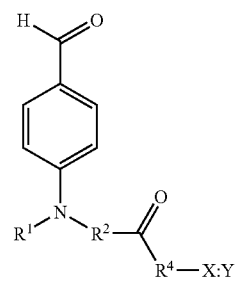

wherein $R^1$ is an alkyl group, $R^2$ is an alkyl group, $R^4$ is a heteroalkyl group, X is a first partner of a strong binding pair and Y is a solid support having a second partner of a strong binding pair on its surface.

Preferably the solution containing the reaction product is neutralized prior to contact with the solid support.

In one embodiment the first partner of the strong binding pair is from avidin and the second partner of the strong binding pair is from biotin. Alternatively the first partner of the strong binding pair is from biotin and the second partner of the strong binding pair is from avidin. In a second embodiment the first partner of the strong binding pair is from biotin and the second partner of the strong binding pair is from streptavidin. Alternatively the first partner of the strong binding pair is from streptavidin and the second partner of the strong binding pair is from biotin.

Preferably the detectable molecule is a monoclonal antibody specific to the biological compound moiety of the complex. Suitably the solid support is a microtitre plate or a treated glass slide.

The present invention also provides a method of purifying an antigen, said method comprising;

1) contacting a pyrrole-containing biological compound with one of;
   a) an optionally labelled derivatizing agent (bound or able to bind to a solid support) wherein the dirivatizing agent forms a reaction product with the biological compound (preferably via covalent attachment thereto) followed by exposure to a detectable molecule which forms a complex with the reaction product; or
   b) an optionally labelled derivatizing agent, not bound to a solid support, wherein the derivatizing agent forms a reaction product with the biological compound (preferably via covalent attachment thereto), followed by exposure to a binding agent bound to a solid support wherein the binding agent is specific to a biological compound in the reaction product; or
   c) a binding agent bound to a solid support, said binding agent being specific to the biological compound, and forming a complex therewith, followed by exposure to an optionally labelled, derivatizing agent, which forms a reaction product with the biological compound moiety of said complex (preferably via covalent attachment thereto); and 2) eluting the biological compound from the solid support.

This method allows easy preparation of an antigen, which can then be used in screening for an antigen detection agent, for example antibody.

Preferably the derivatizing agent for use in the method of purifying an antigen is of the following structure in bound form:

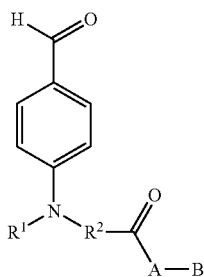

wherein R¹ is an alkyl group, R² is an alkyl group, A is a linking group and B is a solid support.

Preferably the labeled derivatizing agent has the following structure in bound form:

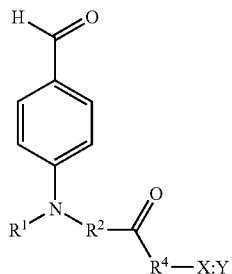

wherein R¹ is an alkyl group, R² is an alkyl group, R⁴ is a heteroalkyl group, X is a first partner of a strong binding pair and Y is a solid support having a second partner of a strong binding pair on its surface.

Preferably the detectable molecule is a monoclonal antibody specific to the biological compound.

Optionally the derivatizing agent is labelled with a radio-label, fluorescent label, enzyme label or the like.

The present invention also provides compounds for use in the method of assaying pyrrole-containing biological compounds.

In one case, the compound is of the following structure:

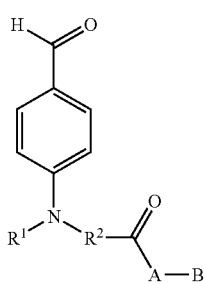

wherein R¹ is an alkyl group, R² is an alkyl group, A is a linking group and B is a solid support.

More preferably the labeled derivatizing agent has the following structure:

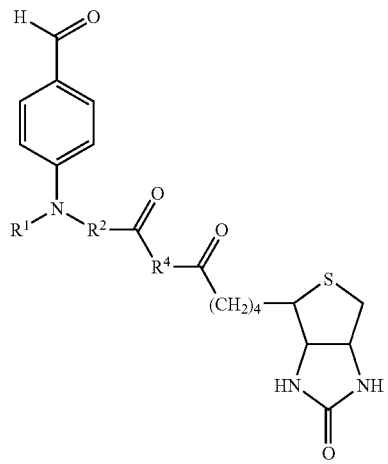

wherein R¹ is a straight-chain alkyl group containing 1 to 10 carbon atoms, R² is a straight-chain alkyl group containing 1 to 10 carbon atoms, and R⁴ is a straight-chain heteroalkyl group containing 2 to 10 carbon atoms and at least 2 heteroatoms.

DESCRIPTION OF THE SPECIFIC EMBODIMENTS

Introduction

The present invention provides methods of assaying pyrrole-containing biological compounds and chemical compositions that can be used in those methods. In Method 1 of the present invention, a biological sample, that may have been processed, is contacted with a solid support bound or able to bind derivatizing agent. Pyrrolic units in the biological sample react with the derivatizing agent, thereby immobilizing components containing the pyrroles on the solid support. The reacted solid support is contacted with a detectable molecule, such as a MAb, which interacts with a portion of the immobilized biological material. Detection of the detectable molecule on the solid support indicates that the biological material contains pyrrolic units.

In Method 2 of the present invention an optionally processed biological sample is contacted with a non-bound, optionally labeled derivatizing agent in solution. The derivatizing agent is suitably labelled with a radio-label, fluorescent label, enzyme label or the like. The derivatizing agent reacts with the pyrrolic units in the biological sample to form a reaction product wherein the reaction product comprises the covalent attachment of the derivatizing agent and the pyrollic units in the biological compound. The solution containing the reaction product is neutralised.

The reaction product may be contacted with a solid support bound MAb specific to the biological sample. The MAb reacts with the reaction product to form a complex immobilized on the solid support. Detection of the labeled molecule on the solid support indicates that the biological material contains pyrrolic units.

In method 3 of the present invention, an optionally processed biological compound is contacted with a derivatizing agent, wherein the derivatizing agent comprises a first binding partner of a strong binding pair, suitably from biotin. The derivatizing agent is in solution. Pyrrolic units in the biological compound react with the derivatizing agent to form a reaction complex. The solution containing the reaction product is neutralised prior to contact with a solid support coated with a second binding partner of the strong binding pair, to form a bound complex with the reaction product. Suitably the second binding partner is from streptavidin. The solid support is then contacted with a detectable molecule, preferably a MAb specific to the biological compound moiety of said complex. The amount of bound biological compound is determined.

Figure 2:
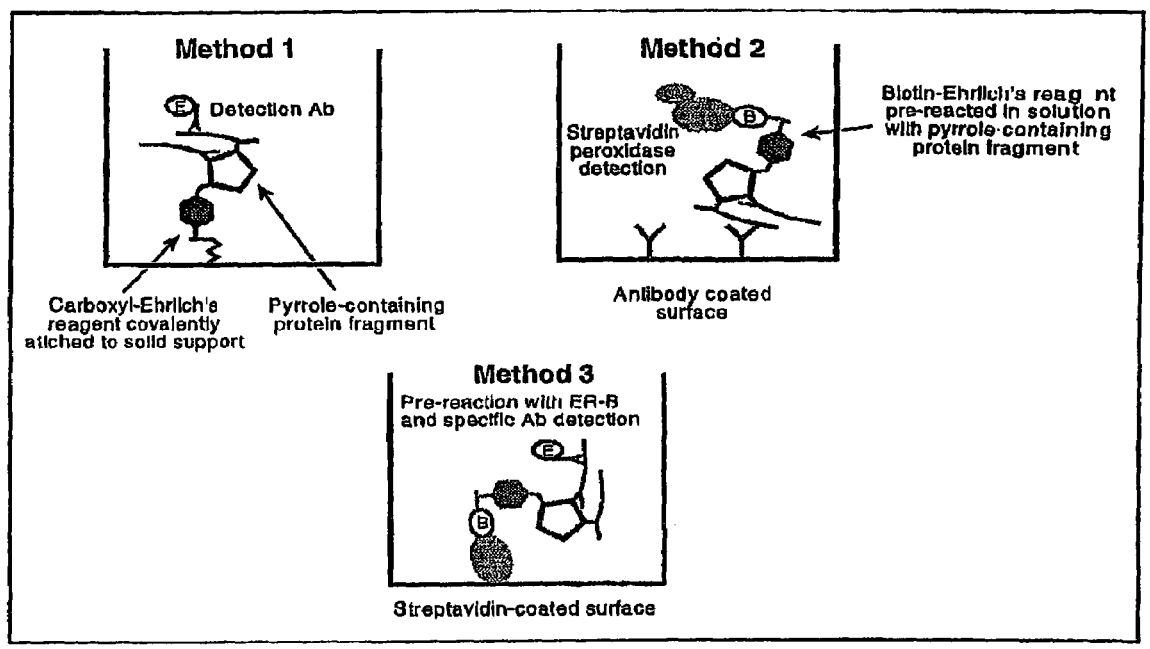
FIG. 2 schematically represents Methods 1, 2 and 3.

FIG. 2 schematically illustrates Methods 1, 2 and 3.

Definitions

"Alkyl group" refers to a straight-chain, branched or cyclic group containing a carbon backbone and hydrogen. Examples of straight-chain alkyl groups include methyl, ethyl, propyl, butyl, pentyl and hexyl. Examples of branched alkyl groups include i-propyl, sec-butyl and t-butyl. Examples of cyclic alkyl groups include cyclobutyl, cyclopentyl and cyclohexyl. The "alkyl" group also refers to alkylene groups.

Alkyl groups are substituted or unsubstituted. In a substituted alkyl group, a hydrogen on the carbon backbone is replaced by a different type of atom (e.g., oxygen, nitrogen, sulfur, halogen). For instance, 2-hydroxyethyl is an ethyl group where one of the hydrogens is replaced by an OH group; 2-chloropropyl is a propyl group where one of the hydrogens is replaced by a Cl group.

"Heteroalkyl group" refers to a straight-chain, branched or cyclic group containing a carbon-heteroatom backbone and hydrogen. Heteroatoms include, without limitation, oxygen, nitrogen and sulfur. The following groups are examples of heteroalkyl groups: —$CH_2OCH_2CH_3$, —NH($CH_2$)$_5$NH— and —NH($CH_2$)$_2$SS($CH_2$)$_2$NHC(O)($CH_2$)$_5$NH—. As with alkyl groups, heteroalkyl groups are substituted or unsubstituted.

"Leaving group" refers to a chemical group that is capable of being displaced in a nucleophilic substitution reaction. Examples of leaving groups include —Cl, —Br, —OC(O)$CH_3$ and —SPh.

"Linking group" refers to a chemical group that connects one chemical group to another. For instance, in the compound $CH_3C(O)$—NH($CH_2$)$_5$NH—$CH_3$, the group —NH($CH_2$)$_5$NH— is a linking group between $CH_3C(O)$— and —$CH_3$.

Types Of Biological Materials To Be Examined

The present method is used to determine the presence of pyrrolic units in biological materials, including pyrrolic crosslinks in collagen extracts. For some time, researchers have proposed that pyrrolic components exist in collagen. See Scott et al., *Biosci. Rep.* (1981) 1:611–618; see also Kuypers et al., *Biochem. J.* (1992) 283:129–136. Only indirect support for the proposal has been available, however, as the isolation and characterization of collagen derived pyrrolic crosslinks has proven difficult.

Experimental results presented herein provide direct confirmation of pyrrolic crosslinks in collagen. See Examples 4 and 5. A series of peptides from human bone collagen enzyme digests were isolated using a solid support bound p-aminobenzaldehyde, indicating the presence of pyrrolic units in the collagen. Analysis of the isolated peptides using mass spectrometry showed that a relatively large number of the peptides possessed masses extremely close to the theoretic masses of complexes derivatized at predominantly the N-telopeptide sites of collagen.

Pyrrolic crosslinks are particularly prevalent in bone collagen where they result from the natural maturation process of the tissue. During resorption of bone by osteoclasts, fragments of collagen crosslinked by pyrroles are released into the circulation. Their concentration in various biological fluids provides an indication of the rates of bone degradation. Increased bone resorption rates are associated with a number of diseases, including, for example, the following: osteoporosis, osteo- and rheumatoid arthritis, and diseases involving abnormalities of vitamin D or parathyroid hormone such as osteomalacia and hyperparathyroidism. By detecting pyrrolic crosslinks using the present invention, therefore, one is able to characterize and monitor such diseases.

Another example of biological materials that can be assayed using the present invention is the isolevuglandins (e.g., levuglandin $E_2$). Isolevuglandins are formed through free radical-mediated oxidation of polyunsaturated fatty acid esters in low-density lipoproteins. These compounds react with various proteins to produce pyrroles in vivo. See Brame et al., *J. Biol. Chem.* (1999) 274:13139–13146; see also Salomon et al., *J. Biol. Chem.* (1999) 274:20271–20280.

Free radical-mediated oxidation has been implicated in a wide variety of human diseases, including atherosclerosis, cancer and neurodegenerative diseases. See B. Halliwell and J. Gutteridge, *Methods Enzymol.* (1990) 186:1–85. Specifically, the oxidative modification of low density lipoproteins is a key step in atherosclerosis etiology. The detection of isolevuglandin derived pyrroles accordingly provides a method for diagnosing and monitoring atherosclerosis.

Proteins modified by non-enzymatic glycosylation reactions constitute a third example of a biological material that can be assayed using the present invention. Threose, primarily derived from the breakdown of ascorbate (vitamin C), represents one instance of this reaction. It is particularly reactive with lysine residues in proteins and forms pyrrolic structures (e.g., formyl threosyl pyrrole) as a result. See R. Nagaraj and V. Monnier, *Biochem. Biophys. Acta* (1995) 1253:75–84.

Detecting formyl threosyl pyrrole is specifically useful for monitoring patients with diabetes. It is also an example of an advanced glycation end-product (AGE). AGEs are associated, for example, with abnormal neurofibrillar structures in Alzheimer's disease, and the presence of increases AGEs in lipoproteins appears to accelerate the oxidative reactions leading to atherosclerosis. Therefore, the detection of formyl threosyl pyrrole provides a method for diagnosing and monitoring those diseases as well.

Methods Of Processing Biological Materials

Subject biological materials assayed using the present method may be unprocessed (e.g., urine, serum or plasma) or processed. A primary goal of processing is the solubilization of the sample.

Where the biological material is a tissue, it is usually de-fatted by two brief extractions (e.g., 15 min.) with acetone or chloroform:methanol (2:1 v/v). Mineralized tissues are, for example, powdered underliquid nitrogen and subsequently demineralized using extraction with 0.5 M EDTA at pH 7.5 for 72–96 hours at 4° C. Connective tissue samples are typically denatured by heating the sample in saline at pH 7.4 for 30 min at 70° C.

Sample solubilization typically involves the use of proteases rather than chemical hydrolysis, as pyrroles exhibit chemical instability under certain conditions. Where proteases are used, a sample is treated with a suitable proteolytic enzyme (e.g., trypsin) at a suitable temperature (e.g., 37° C.). Examples of other enzymes one can use to solubilize a biological material include chymotrypsin, pronase, pepsin, proteinase K and members of the cathepsin family (B, L, N or K). For any chosen enzyme, one of ordinary skill can readily determine a suitable reaction buffer pH and temperature.

Derivatizing Agents

The deritivizing agents used in the present assay are p-amino benzaldehyde derivatives used in the present assay are of the structures 4 and 5. $R^1$ in the structures is an alkyl group; $R^2$ is an alkyl group;

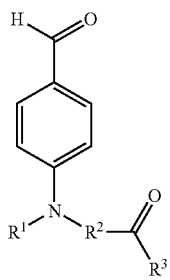

4

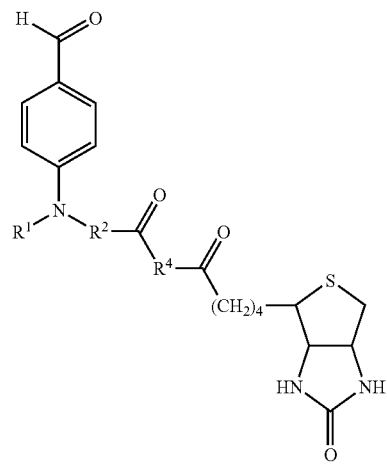

5

$R^3$ is a hydroxyl group or leaving group; and, $R^4$ is a heteroalkyl group.

The substituent $R^1$ is preferably a straight-chain alkyl group containing 1 to 10 carbon atoms. It is more preferably a straight-chain alkyl group containing 1 to 5 carbon atoms. Most preferably, $R^1$ contains 1 carbon atom (i.e., —CH$_3$).

The substituent $R^2$ is preferably a straight-chain alkylene group containing 1 to 10 carbon atoms. It is more preferably a straight-chain alkylene group containing 1 to 5 carbon atoms. Most preferably $R^2$ contains 2 carbon atoms (i.e., —CH$_2$CH$_2$—). The substituent $R^3$ is preferably —OH, —OR$^5$ (where $R^5$ is a straight chain alkyl such as methyl), —Cl or SR$^5$. It is more preferably —OH or —OR$^5$. Most preferably $R^3$ is —OH.

The substituent $R^4$ is preferably a straight-chain heteroalkyl group containing 2 to 10 carbon atoms and at least 2 heteroatoms. It is more preferably a straight-chain heteroalkyl group containing 4 to 10 carbon atoms and at least 2 nitrogen atoms. Most preferably $R^4$ is —NHCH$_2$CH$_2$CH$_2$CH$_2$CH$_2$NH— or —NHCH$_2$CH$_2$SSCH$_2$CH$_2$NHC(O)—CH$_2$CH$_2$CH$_2$CH$_2$CH$_2$N—.

Examples of three preferred derivatizing agents are p-amino benzaldehyde derivatives are shown as compounds 6, 7 and 8:

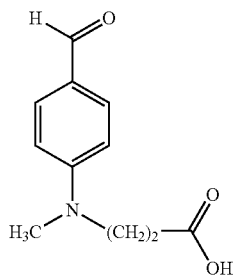

6

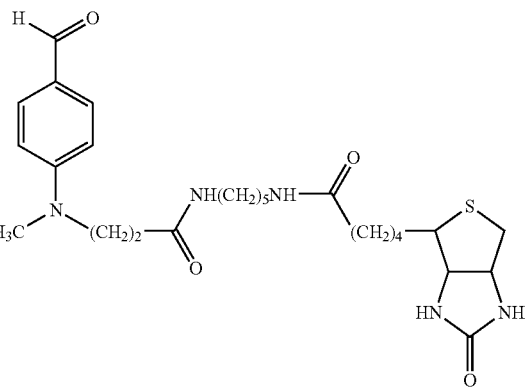

7

-continued

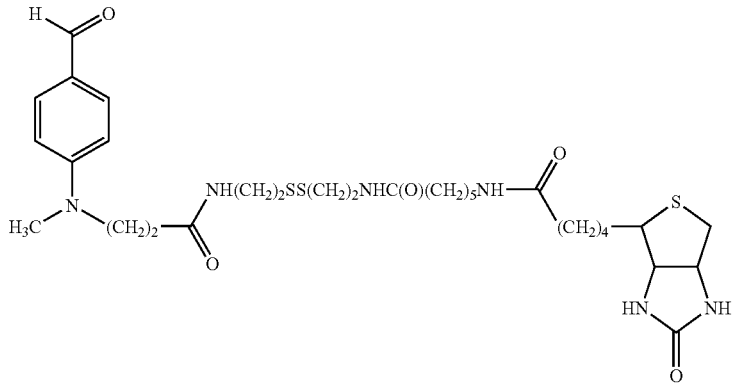

8

Modes Of Attachment To A Solid Support

The derivatizing agent is attached to the solid support through either a covalent bond or a noncovalent interaction. A derivatizing agent in bound form attached to solid support through a covalent bond is represented by compound 9; a derivitizing agent in bound form attached to a solid support through a noncovalent interaction is represented by compound 10:

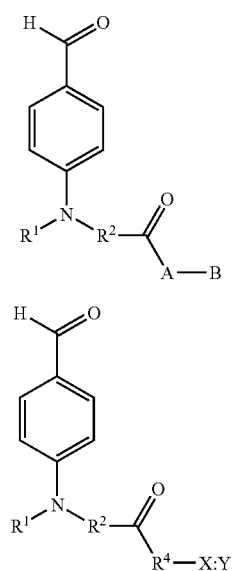

9

10

The substituents of compound 9 are defined as follows: $R^1$ is an alkyl group; $R^2$ is an alkyl group; A is a linking group and B is a solid support. Preferably, $R^1$ and $R^2$ are alkyl groups containing 1 to 10 carbon atoms and A is a heteroalkyl group.

More preferably, $R^1$ and $R^2$ are alkyl groups containing 1 to 5 carbon atoms and A is a heteroalkyl group comprising at least 1 nitrogen atom. Most preferably, $R^1$ is —$CH_3$ and $R^2$ is —$CH_2CH_2$—. The substituents of compound 10 are defined as follows: $R^1$ is an alkyl group; $R^2$ is an alkyl group; $R^4$ is a heteroalkyl group; X is a first partner of a strong binding pair and Y is a solid support having a second partner of a strong binding pair on its surface. Preferably, $R^1$ and $R^2$ are alkyl groups containing 1 to 10 carbon atoms and $R^4$ is a straight-chain heteroalkyl group containing 2 to 10 carbon atoms and at least 2 heteroatoms. More preferably, $R^1$ and $R^2$ are alkyl groups containing 1 to 5 carbon atoms, $R^4$ is —$NH(CH_2)_5NH$— or —$NH(CH_2)_2SS(CH_2)_2NHC(O)$ $(CH_2)_5NH$—. Most preferably, $R^1$ is —$CH_3$ and $R^2$ is —$CH_2CH_2$—.

Where a covalent bond is used for attachment, a surface is typically derivatized to afford a reactive functional group such as an alcohol or amine. For instance, compound 6 is coupled to a Nunc Covalink™ plate, available from Nalge Nunc International, through the formation of an amide bond with a C8-primary amine. See www.nalgenunc.com. A second example of a suitable solid support is a DNA-BIND™ surface, available from Corning. See www.scienceproducts.corning.com. One reacts a bifunctional compound, such as 1,5-diaminopentane, with the surface to provide available amine groups for covalent attachment. A compound such as 6, which contains a carboxylic acid, is coupled to the surface groups through the formation of an amide bond. A third example of a solid support is a glass substrate. A glass slide is treated with aminopropyl-triethoxysilane to provide a glass substrate containing a reactive amine across its surface. See U.S. Pat. No. 5,919,523. The derivatized slide is reacted with compound such as 6 in the presence of a suitable reagent that induces amide bond formation. Where a noncovalent interaction is used for attachment, a compound containing one partner of a strong binding pair is adhered or bonded to the solid support. The other partner of the pair is covalently attached to a derivatizing agent to form a conjugate. When the conjugate is contacted with the solid support, a strong interaction (e.g., one or more hydrogen bonds) immobilizes the conjugate on the support.

An example of a strong binding pair is a biotin:avidin complex. (A biotin:streptavidin complex is another example.) Typically, a support surface is derivatized to include biotin or avidin. Avidin coated polystyrene plates (i.e., Reacti-Bind™ NeutrAvidin™ coated plates) are available, for instance, from Pierce. See www.piercenet.com. The avidin coated plate is contacted with a biotin containing p-aminobenzaldehyde derivative such as compound 7. The resulting biotin-avidin complex serves to attach compound 7 to the solid support through noncovalent interactions.

Examples Of Different Assay Formats

The method of assaying pyrrole-containing biological compounds is typically run in a multi-well plate (e.g., 96-well plate), but other assay formats are also used. The method is also performed using a strip format, where a derivatizing agent is immobilized on the strip surface. A third exemplary format involves the use of a polymeric bead (e.g., polystyrene bead) on which a derivatizing agent is immobilized. Yet another format involves the use of microarray or chip technology; use with surface plasmon resonance technology.

Contact Of Extract/Isolate With Detection Compound

To perform a method of the present invention, a biological fluid or processed biological material is contacted with a solid support bound derivatizing agent. The biological material may be solubilized in a suitable solvent to form a solution prior to the contact. When a multi-well format is used, for example, the solution and any additional elements readily discernable to one of ordinary skill in the art is added to one or more wells. For the strip format, a strip is dipped into a solution containing the biological material; and, for the bead format, a vial or tube is used to mix the beads and the solution.

Regardless of assay format, contact between a pyrrole-containing biological material and the support bound derivatizing agent induces a coupling reaction. The result of the reaction is a covalent bond between the biological material and the derivatizing agent. This serves to immobilize the pyrrole-containing biological material on the solid support.

When desired, the solid support bound biological material is washed with at least one suitable solvent to remove impurities from the reaction medium. The solid support is typically dried after a washing step. A variety of drying techniques are used, including air drying, drying under reduced pressure and thermal drying.

Methods Of Detection Using A Detectable Molecule

In a method of the present invention, the immobilized material is contacted with a detectable molecule. The detectable molecule specifically binds to a portion of a targeted biological material. If the material on the solid support is not the targeted material, the detectable molecule will not bind to it with high affinity.

The detectable molecule can bind to the targeted biological material through either covalent or noncovalent bonds. Typically, the detectable molecule is a polyclonal, monoclonal or phase library-derived antibody that binds to the biological material through noncovalent bonds. Preferably, it is a monoclonal antibody.

The detectable molecule is typically detectable in one of three ways: 1) it contains functionality one can observe; 2) it induces a chemical reaction that produces an observable product; or 3) it interacts with a second molecule that either contains functionality one can observe or induces a chemical reaction that produces an observable product. Functionality one can observe includes chemical groups that exhibit a measurable effect upon stimulation. For instance, the following chemical groups exhibit such an effect: a chemical group that absorbs light at a certain wavelength (a chromophore) and a chemical group that fluoresces upon exposure to a particular wavelength of light. A chemical reaction that produces an observable product includes, for example, a reaction producing a fluorescent compound, a luminescent compound or a chromophoric compound.

Where the targeted biological material is collagen derived pyrrole crosslinks, an example of a detectable molecule is a monoclonal antibody (NTP) raised against a synthetic octapeptide comprising part of the sequence of the α2(I) N-terminal telopeptide. The NTP antibody is contacted with the immobilized biological material. A secondary antibody (goat anti-mouse IgG-peroxidase conjugate) is introduced; which interacts with a portion of the NTP antibody. Upon addition of 3,3', 5,5'-tetramethyl-benzidine dihydrochloride and hydrogen peroxide, a chromophoric compound exhibiting an absorbance at 450 nm is produced. See Example 6.

Contact of Extract/Isolate with Detection Compound

To perform Method 2 or 3 of the present invention, a biological fluid or processed biological material is contacted with a labeled derivatizing agent in solution. The derivatizing agent is labeled with a labeling molecule. Any suitable solvent as known by a person skilled in the art may be used. A coupling reaction between pyrrole-containing biological material results in a reaction product comprising the derivatizing agent covalently bonded to any pyrrole-containing biological material.

Methods of Detection Using a MAb

In Method 2 of the present invention the reaction product is immobilised by contact of the solution with a MAb bound on a solid support.

EXAMPLE 1

Preparation of Compound 6.

N-Methyl-N-cyanoethyl-4-amino benzaldehyde (available from Enterwin Chemicals, China or Sigma-Aldrich, USA) (150 mg) was dissolved in 7.5 M NaOH, 6% $H_2O_2$ (5 ml) and refluxed for 2 hours. The hydrolysate was acidified by addition of concentrated HCl, dried under vacuum and redissolved in ethanol (1.5 ml). An aliquot of the solution (1 ml) was added to 0.2 M NaOH (1 ml) and applied to an anion exchange column (Bio-Rad AG 1-X8; 2 ml, pretreated with 2 M HCl, 2 M NaOH and equilibrated with water). The column was washed with water (12 ml) before elution of the bound material with 2 M HCl. The eluent was dried under vacuum and the residue resuspended in water (1 ml). A small amount of residue (soluble in ethanol but containing no compound 6) was removed after which the aqueous fraction was dried under vacuum (yielding 7 mg of material) and redissolved in 0.1% trifluoroacetic acid (1 ml). Aliquots (100 μl) of the material was chromatographed on a Waters RCM Prep-Pak® $C_{18}$ column (25 mm×100 mm, 10 μm) pumped at 4 ml/min. The buffers used were 0.1% TFA (buffer A) and 70% acetonitrile, 0.1% TFA (buffer B) with a gradient of 5 minutes at 5% B followed by a linear increase to 70% B over 35 minutes. Monitoring at 330 nm showed a single major peak which eluted at 28.3 min. Fractions corresponding to the peak were pooled and dried under vacuum (yield=3 mg). Analysis of the material by electrospray mass-spectrometry in negative-ion mode using a MAT 900 mass spectrometer (Finnigan MAT, Bremen, Germany) revealed the major ion as [M−H]=206.2 which corresponds to the expected value for N-methyl-N-propionic acid-4-amino benzaldehyde $M_r$ 207.2.

EXAMPLE 2

Preparation of compound 7

Compound 6 (3 mg) was dissolved in water (3 ml) and biotin-pentyl amine (30 mg; Pierce) was added. A solution of 1-ethyl-3-(3-dimethylamino-propyl)carbodiimide/N-hydroxysuccinimide (0.035 M/0.028 M respectively; 3 ml) was added and heated to 50° C. for 4 h. The resulting solution was dried under vacuum and chromatographed using the preparative RCM Prep-Pak® column described in Example 1. The gradient applied was 20% B for 5 min followed by a linear increase to 60% B over 30 min. Two major components were detected, one eluting at 15 min. (unreacted acid) and one eluting at 18 min. The component eluting at 18 min was analyzed by positive-ion electrospray mass-spectrometry and showed [M+H] of 518.7 and [M+Na] of 540.6. These values corresponded to the calculated $M_r$ of compound 7 of 517.7. Compound 7 reacted with pyrrole carboxylic acid in 4 M HCl to give a characteristic pink color absorbing at 573 nm.

EXAMPLE 3

Preparation of Compound 8

Compound 6 (1 mg) was dissolved in 0.1 M MES buffer pH 5 (1 ml) and a ten-fold molar excess of cystamine ($H_2N(CH_2)_2SS(CH_2)_2NH_2$) was added. The solution pH was adjusted to 5 using HCl, and a solution of 1-ethyl-3-(3-dimethylamino-propyl)-carbodiimide/N-hydroxysuccinimide (0.035 M/0.028 M respectively; 1 ml) was added. The solution was heated to 50° C. for 4 h. The resulting aminated derivative was purified by HPLC, eluting with 10 mM TFA and an acetonitrile gradient (monitoring 330 nm). Biotinylation of the aminated derivative was performed using succinimide-LC-biotin (Pierce) according to the manufacturer's instructions and again purified by HPLC. Structure 8 was confirmed by MALDI-TOF mass spectrometry.

EXAMPLE 4

Reaction of Compound 7 with a Bone Digest

De-fatted human bone (7 g) was powdered in a Spex freezer-mill in liquid nitrogen. The resultant powder was decalcified by 3×2-day extractions in 0.5 M EDTA, pH 8 at 4° C., washed with water and lyophilized. The decalcified bone powder (1.1 g) was suspended in 0.1 M citrate buffer, pH 5, heated to 70° C. for 1 hour to denature the triple-helical structure and allowed to cool to 45° C. Papain (100 U) was added, and the digest was incubated for 4 hours. The pH of the digest was adjusted to 7.4 by the addition of 1 M Tris, and the temperature was lowered to 37° C. for an overnight digestion with protease type X (100 U). The completed digest (estimated as 110 μM collagen by total pyridinium crosslink content) was frozen, lyophilized and suspended in water (7 ml).

After the addition of compound 7 (50 μg) to the bone digest (500 μl), the mixture was acidified by the addition of 12 M HCl (250 μl). During incubation for 30 min at room temperature, the solution turned cherry-pink in color, and spectrometry showed the presence of an absorption maximum at 571.7 nm (characteristic of product from reaction of 4-dimethylamino benzaldehyde with pyrrole). The acid was neutralized by the addition of 12 M NaOH (approx. 220 μl) followed by 40 mM phosphate buffer (20 ml).

EXAMPLE 5

Isolation of Conjugation Product Between Compound 7 and Pyrrolic Peptides

A monomeric avidin column (5 ml) was prepared according to manufacturer's (Pierce) instructions. The reacted bone digest of Example 4 at neutral pH was added slowly to the column, which was then washed with 6 column volumes of PBS followed by 1 column volume of water. The biotinylated material was eluted at about 1 ml/min with 1 M acetic acid adjusted to pH 2.5 with ammonia, and 8 fractions (5 ml) were collected.

Estimation of biotinylated compounds by competitive ELISA. In order to assess the efficiency of the monomeric avidin column (Example 5), a competitive ELISA was developed. Immulon 4 immunoassay plates were coated with streptavidin (25 nM) in PBS for 2 hours at 37° C. Samples or standards in PBS 0.1% Tween, 0.5% fat-free milk powder (FFMP; 110 μl) were added to biotinylated peroxidase (Sigma; 10 ng/ml; 110 μl) in PBS Tween, 0.5% FFMP in a U-bottomed 96-well plate. The mixed samples were transferred to the washed, streptavidin-coated plate and incubated for 90 min at 37° C. After washing the plate 3 times with PBS/0.1% Tween, the peroxidase substrate (200 μl) tetramethyl-benzidine dihydrochloride (TMB) was added (0.1 mg/ml) in 0.05 M citrate/phosphate buffer pH 5, 0.012% v/v hydrogen peroxide. The reaction was stopped by the addition of 3 M sulphuric acid (50 μl) after 15 min.

Analysis of isolated material by HPLC. Material eluted from the avidin column was reduced in volume (100 μl) and chromatographed on a reversed phase HPLC column (4.6× 100 mm; $C_{18}$; particle size 3 μm). The column was equilibrated with 0.1% TFA (buffer A), and peptides were eluted over 35 min with linear gradients formed with 70% acetonitrile, 0.1% TFA (buffer B). The eluent was monitored at 214 nm, 280 nm and at 330 nm. Each fraction from the HPLC was dried and redissolved in water (2 μl). An aliquot (1 μl) was mixed with α-cyano-4-hydroxy-cinnamic acid (1 μl of a 10 mg/ml solution in 70% acetonitrile 0.1% TFA), dried onto a sample plate and analyzed by MALDI-TOF mass spectrometry (Voyager-DE; Applied Biosystems) calibrated externally using bradykinin.

Figure 1:
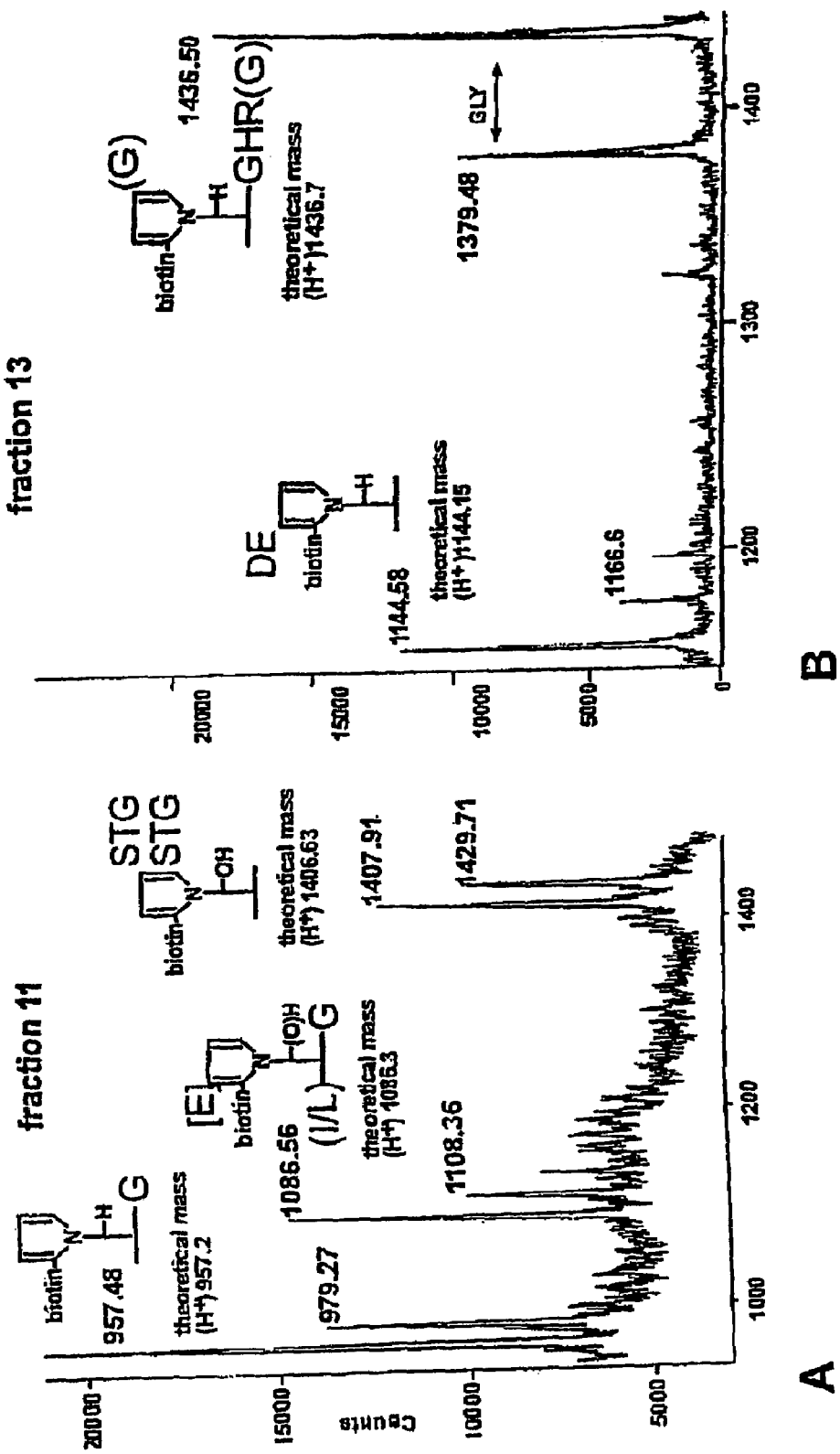
FIGS. 1a–1i show mass spectrometry spectra of pyrrole crosslink-containing peptides.

The MALDI-TOF mass spectrometry spectra of each fraction is shown in FIG. 1. As there were insufficient quantities of many of the smaller peptides to obtain amino acid composition data, some ambiguities in their structural assignments did arise. In particular, the mass difference between Glu and Ile/Leu is equivalent to an additional hydroxyl group and, for the isolated peptide with $M_r$=1086 (FIG. 1a), the ambiguity is due to the possible presence of a hydroxylated crosslink. Thus, this peptide may contain Gly and Glu (from either the C- or N-telopeptides of the α1 chain) or, for a hydroxylated crosslink, a Gly residue linked with either Ile (from the α1 helix) or a leucine (from the α2 helix). Even where the amino acid composition is known, the precise location of the residues may not be clear, as in the case of the peptide with $M_r$=957 (FIG. 1a) containing the biotinylated pyrrole with a single Gly residue. This residue is shown in a helical position (which could be at the N- or C-terminal overlap sites) but could also be derived from the α2(I) N-telopeptide: this peak may contain a mixture of Gly-containing peptides from the different locations. The Mr=1029 peptides shown in FIGS. 1e and 1g could have the same alternatives of glutamate or hydroxylated pyrrole-leucine/isoleucine.

The peaks corresponding to a loss of Gly (FIG. 1b, 1c) are probably losses due to the energy of the laser-desorption rather than discrete peptides, but these peaks provide additional evidence for the peptide structures proposed. The structures of the larger peptides shown in the other panels are unambiguous.

EXAMPLE 6

Detection of Pyrrole Crosslinks (Method 1)

The carboxyl-Ehrlich derivative was coupled to a Nunc Covalink® plate via a C8-primary amine group. After adding the derivative to the plate (250 pmole/well in 100 μl MES buffer, pH 4.5) followed by 100 µl of 1-ethyl-3-(3-dimethylamino-propyl)carbodiimide/N-hydroxysuccinimide (0.035M/0.028M respectively), the plate was heated to 50° C. and left overnight at room temperature. The plate was aspirated and washed with 4M HCl and 3 times with water. Each well coupled the equivalent of 66 pmoles of the reagent and the coupling was confirmed using HPLC.

Samples (110 µl), prepared in a separate plate, were acidified by the addition of 8M HCl (110 µl). The acidified samples (200 µl) were then added to the Ehrlich reactive plate and agitated for 1 hour at room temperature. The plate was aspirated and washed 3 times in 4 M HCl, 3 times in water and finally 3 times in PBS/0.1% Tween; 10 mM lysine, 0.5% fat-free milk powder (assay buffer). The antibodies used were a monoclonal antibody (NTP) raised against the $\alpha 2$ (I) telopeptide (1:1000 dilution) or affinity-purified, polyclonal antibodies raised against the isoaspartyl $\alpha 2$ (I) telopeptide (1:250 dilution). After incubation for 17 hours at 4° C., the plate was washed 3 times with PBS-Tween and incubated for 1 hour with secondary antibodies, goat anti-mouse IgG-peroxidase conjugate, used at a dilution of 1:4000. The plate was washed 3 times with PBS-Tween, and 200 µl of peroxidase substrate, 3,3',5,5'-tetramethyl-benzidine dihydrochloride (TMB) is added (0.1 mg/ml) in 0.05 M citrate/phosphate buffer, pH 5, containing 0.012% v/v hydrogen peroxide. The reaction is stopped by the addition of 3 M sulfuric acid (50 µl), and the absorbance was measured at 450 nm using a Dynatech MR 7000 plate reader.

Figure 3:
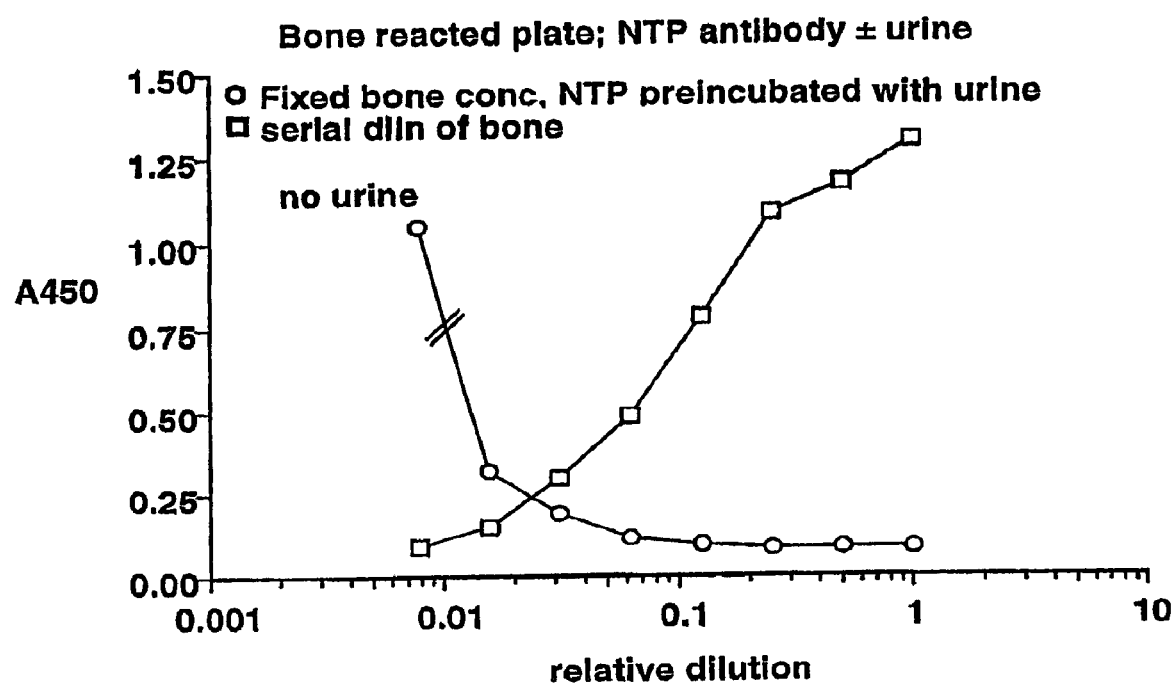
FIG. 3 shows the difference of pyrrole capture of bone peptides at different dilutions.

Using the pyrrole-capture assay, serial dilutions of a bone digest (starting at ~1.0 nmole/well collagen) reacted in the Ehrlich plate gave progressively decreasing reactivity with NTP antibody (FIG. 3). At a fixed concentration (0.125 nmole/well) of pyrrole-crosslinked bone peptides on the plate, preincubation of the NTP antibody with serial dilutions adolescent-human urine gave essentially complete inhibition of colour development.

Figure 4:
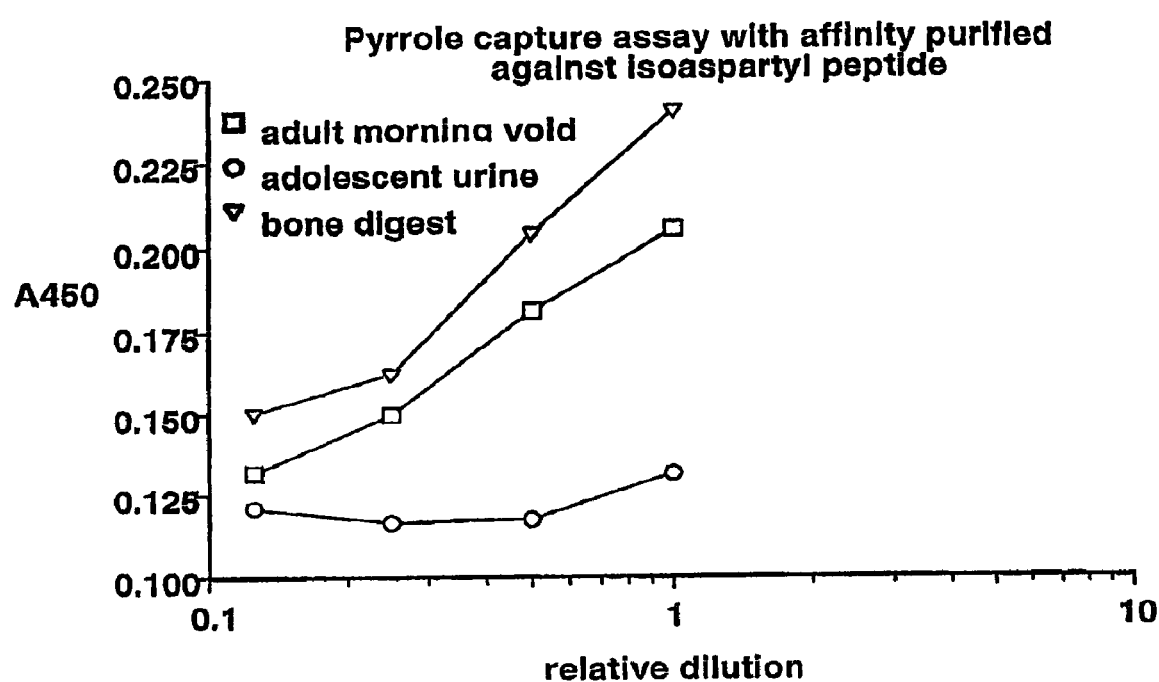
FIG. 4 shows pyrrole capture at different dilution of biological sample using detection antibodies specific for isoaspartyl telopeptides.

When pyrrole crosslink-containing peptides in urine from an adolescent were reacted with the plate, the NTP antibody failed to detect any telopeptide (FIG. 4). A possible explanation for this is that the large quantities of non-isomerised telopeptide found in urine at this age may not be extensively crosslinked. This is supported by the fact that the polyclonal antibody raised against the isoaspartyl rearranged peptide did show reactivity towards captured peptides in urine from an older subject (30 years), see FIG. 4.

Figure 5:
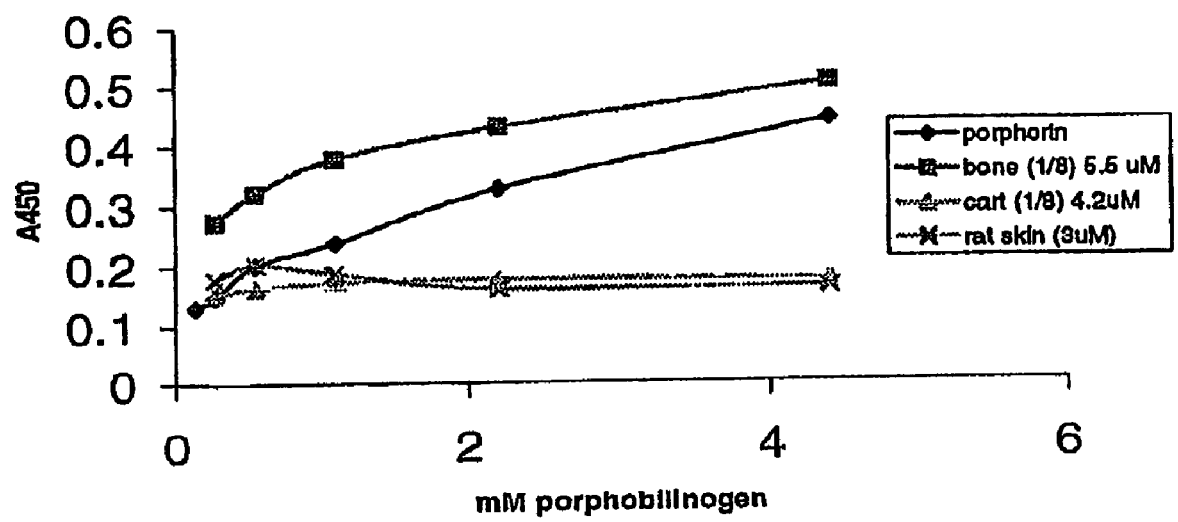
FIG. 5 shows pyrrole capture assay for digested and immobilized collagen-containing tissues.
Figure 6:
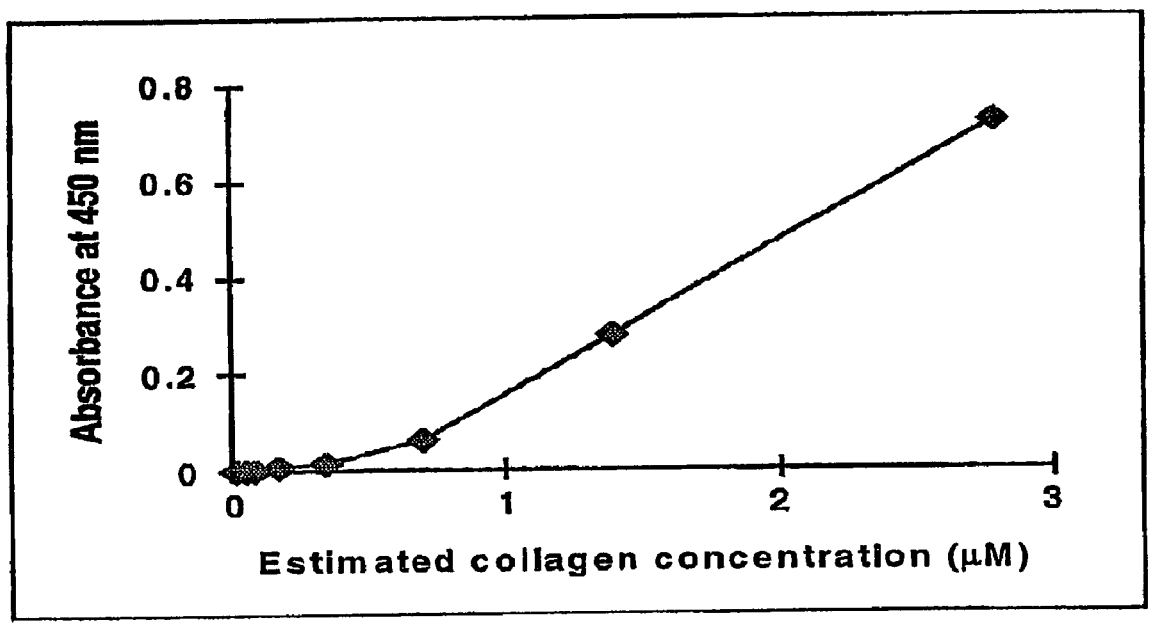
FIG. 6 shows the results for a serial dilution of biotin-ER reacted bone digest or a streptavidin coated plate detected with NTP monoclonal antibody.

The specificity of the assay was demonstrated by showing that peptides derived from cartilage and skin, which have no pyrrolic crosslinks, gave very little reaction in the assay compared to the bone digest and a phorphobilinogen standard (FIG. 5).

EXAMPLE 7

Detection of Pyrrole-containing Peptides from Enzyme Digests of Bone (Method 2)

A tryptic digest of demineralized human bone (0.5 ml containing approximately 5 µM collagen) was reacted with biotinylated Ehrlich's reagent (50 µg; 0.1 µmoles) in 3MHCl for 30 min at room temperature. The sample was neutralized by the addition of 2M NaOH and diluted to 10 ml in phosphate buffered saline, pH 7.5 (PBS) containing 0.1% Tween 20. Serial (×2) dilutions of this pre-reacted mixture were prepared in PBS-Tween for addition to the detection plate.

The detection microtitre plate was coated with a monoclonal antibody (NTP) recognizing an octapeptide sequence containing the cross-linking region of the N-telopeptide of collagen type I $\alpha 2$ chain. In order to gain the appropriate orientation of the antibody, the plate was initially coated (3 hours at room temperature) with anti-mouse IgG (raised in donkey) by adding to each well 0.2 ml of a solution containing 1µg/ml protein in PBS. After washing 3 times with PBS-0.05% Tween 20, the NTP antibody (1 µg/ml in PBS) was added and reaction allowed to proceed for 1 hour at room temperature. The plate was again washed 3 times with PBS-Tween.

Serial dilutions of the pre-reacted mixture were added to the coated plate and incubated at room temperature for 2 hours. The plate was washed 3 times with PBS-Tween and the biotin-pyrrole detected by the addition of streptavidin-horseradish peroxidase (Amersham plc, Little Chalfont, UK) diluted 1:2000 in PBS-Tween. After 1 hour the plate was washed 3 times in PBS-Tween and the colour developed by the addition of 200 µl of peroxidase substrate, 3,3',5,5'-tetramethyl-benzidine dihydrochloride (TMB) is added (0.1 mg/ml) in 0.05 M citrate/phosphate buffer, pH 5, containing 0.012% v/v hydrogen peroxide. The reaction is stopped by the addition of 3 M sulfuric acid (50 µl), and the absorbance was measured at 450 nm using a Dynatech MR 7000 plate reader.

EXAMPLE 8

Detection of Pyrrole-containing Peptides from Enzyme Digests of Bone (Method 3)

Biotinylated Ehrlich's reagent was reacted with tryptic peptides of human bone collagen as described for Method 2.

For the detection plate, high-binding microtitre plates (Immunlon 4) were coated with streptavidin (1 µg/ml in PBS) by incubating for 3 hours at 37° C. The plates were washed 3 times with PBS-Tween and any remaining binding sites were blocked by incubation at room temperature for 1 hour with 3% bovine serum albumin in PBS-Tween. The plate was again washed 3 times with PBS-Tween. Alternatively, ready coated plates are available commercially from several sources, such as Streptavidin-coated Combiplates from Thermo Labsystems, Basingstoke, UK.

Serial dilutions of the pre-reacted mixture were added to the streptavidin coated plate and incubated at room temperature for 2 hours. The plate was washed 3 times with PBS-Tween and, after the addition of NTP monoclonal antibody (1:1000 dilution in PBS-Tween), the plate was incubated at 4° C. for 18 hours. The plate was washed 3 times with PBS-Tween and incubated for 1 hour with secondary antibodies, goat anti-mouse IgG-peroxidase conjugate, used at a dilution of 1:4000. After washing the plate 3 times with PBS-Tween, colour development with TMB and recording optical densities at 450 nm using the plate reader were done as described previously.

EXAMPLE 9

Preparation of Pyrrole Containing Antigens from Bone Collagen Peptides

Peptides were prepared from powdered, decalcified human bone by digestion with cathepsin K. The bone (10 mg) was suspended in 1.0 ml of 50 mM sodium acetate buffer, pH 5.0, containing 2 mM EDTA and 2 mM dithiothreitol and, after the addition of 0.1 mg recombinant cathepsin K dissolved in 100 μl PBS, digestion was continued for 24 hours at 37° C. with gentle agitation. The digest was centrifuged (13,000 g) to remove any undigested tissue, and the supernatant solution was desalted on a column (1.0×12 cm) of Sephadex G25 equilibrated and eluted with 0.2M acetic acid. Pooled fractions containing the bone peptides were lyophilised and reacted with biotinylated, disulphide Ehrlich's reagent (compound 8; 0.1 mg; 0.2 μmoles) in 3M HCl at room temperature for 30 mins. The solution was neutralized by the addition of 2 M NaOH and diluted to 10 ml with PBS.

The bone digest Ehrlich conjugate was applied to a 5 ml column of immobilized avidin (Pierce Chemical Co) prepared according to the manufacturer's instructions, and the column washed with PBS containing 10 mM dithiothreitol and located by monitoring the column effluent at 230 nm. Pooled fractions were dialysed against PBS to remove reducing agent. This material was mixed with an equal volume of adjuvant and used directly for immunization of rabbits and mice.

The invention claimed is:

1. A method of assaying pyrrole-containing biological compounds in a sample, the method comprising:
   i) contacting the sample with:
      a) an Ehrlich's reagent covalently attached to a solid support through the amine moiety of the Ehrlich's reagent, wherein the Ehrlich's reagent forms a reaction product with the biological compound, followed by exposure of the reaction product to a first antibody which forms a complex with the reaction product; and
   ii) determining the biological compound by detecting the complex.

2. The method according to claim 1, wherein the Ehrlich's reagent has the following formula

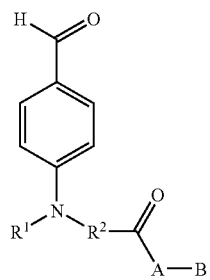

wherein $R^1$ is an alkyl group, $R^2$ is an alkylene group, A is a linking group and B is a solid support.

3. The method according to claim 2, wherein $R^1$ is a straight-chain alkyl group containing 1 to 10 carbon atoms, and $R^2$ is a straight-chain alkylene group containing 1 to 10 carbon atoms.

4. The method according to claim 2, wherein A is a heteroalkylene group.

5. The method according to claim 1, wherein the antibody is a monoclonal antibody.

6. The method according to claim 3, wherein $R^1$ is a straight-chain alkyl group containing 1 to 5 carbon atoms and $R^2$ is a straight chain alkylene group containing 1 to 5 carbon atoms.

7. The method according to claim 4, wherein A is a heteroalkylene group comprising at least one nitrogen atom.

8. The method according to claim 1, wherein the complex is detected with a second antibody that binds to the first antibody.

9. The method according to claim 6, wherein the Ehrlich's reagent is of the following structure:

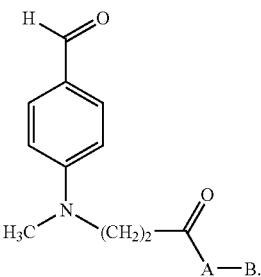

10. The method according to claim 9, wherein A is a heteroalkyl heteroalkylene group containing at least one nitrogen atom.

11. A method of assaying pyrrole-containing biological compounds in a sample, the method comprising:
    a) contacting the sample with a biotinylated Ehrlich's reagent in solution to form a reaction product therewith, followed by exposure of the reaction product to a first antibody bound to a solid support wherein the first antibody forms a complex with the reaction product, and wherein the biotinylated Ehrlich's reagent comprises a linker which links the Ehrlich's reagent to biotin through the amine moiety of the Ehrlich's reagent; and
    b) determining the biological compound by determining the complex.

12. The method according to claim 11 wherein the solution containing the reaction product is neutralized prior to contact with the binding agent.

13. A method of assaying pyrrole-containing biological compounds in a sample, the method:
    a) contacting the sample with a biotinylated Ehrlich's reagent in solution to form a reaction product wherein the Ehrlich's reagent is linked through the amine moiety of the Ehrlich's reagent to biotin;
    b) contacting the reaction product with a solid support coated with strepavidin or avidin, wherein the reaction product is bound to the solid support; and
    c) determining the bound biological compound; thereby assaying the pyrrole-containing biological compound.

14. The method according to claim 13 wherein the reaction product is further contacted with a first antibody that binds to the reaction product to form a complex, and the complex is determined by a second antibody that is labeled and binds to the first antibody.

15. The method of claim 13, wherein the Ehrlich's reagent has the following structure:

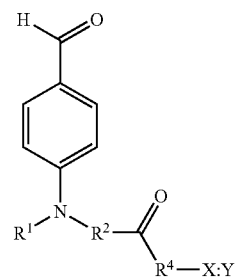

wherein R¹ is an alkyl group, R² is an alkylene group, R⁴ is a heteroalkylene group, X is biotinyl and Y is streptavidin or avidin attached to a solid support.

16. The method according to claim 15, wherein R¹ is a straight-chain alkyl group containing 1 to 10 carbon atoms, and R² is a straight-chain alkylene group containing 1 to 10 carbon atoms.

17. The method according to claim 15, wherein R⁴ is a straight-chain heteroalkylene group containing 2 to 10 carbon atoms and at least 2 heteroatoms.

18. The method according to claim 15, wherein Y is a solid support having avidin on its surface.

19. The method according to claim 14, wherein the first antibody is a monoclonal antibody.

20. The method according to claim 15, wherein R¹ is a straight-chain alkyl group containing 1 to 5 carbon atoms, and R² is a straight chain alkylene group containing 1 to 5 carbon atoms.

21. The method according to claim 14, wherein the second antibody is a monoclonal antibody.

22. The method according to claim 15, wherein the derivatizing agent, in bound form, is of the following structure:

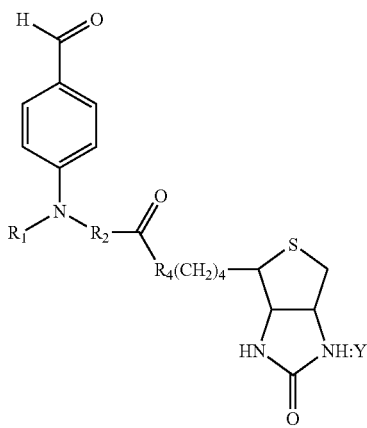

wherein R¹ is a straight-chain alkyl group containing 1 to 5 carbon atoms, R² is a straight-chain alkylene group containing 1 to 5 carbon atoms, R⁴ is a straight-chain heteroalkylene group containing 2 to 10 carbon atoms and at least 2 heteroatoms, and Y is a solid support having avidin or streptavidin on its surface.

23. The method according to claim 22, wherein R¹ is —CH₃, R² is —CH₂CH₂— and R⁴ is —NH(CH₂)₅NH— or —NH(CH₂)₂SS(CH₂)₂NHC(O)(CH₂)₅NH—.

24. The method according to claim 23, wherein R⁴ is —NH(CH₂)₅NH—.

25. The method of claim 11, wherein the Ehrlich's reagent has the following structure:

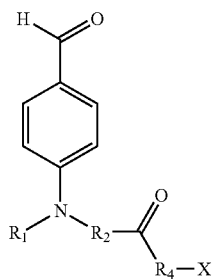

wherein R¹ is an alkyl group, R² is an alkylene group, R⁴ is a heteroalkylene group, and X is biotinyl.

26. The method according to claim 25, wherein R¹ is a straight-chain alkyl group containing 1 to 10 carbon atoms, and R² is a straight-chain alkylene group containing 1 to 10 carbon atoms.

27. The method according to claim 25, wherein R⁴ is a straight-chain heteroalkylene group containing 2 to 10 carbon atoms and at least 2 heteroatoms.

28. The method according to claim 11, wherein the first antibody is a monoclonal antibody.

29. The method according to claim 25, wherein R¹ is a straight-chain alkyl group containing 1 to 5 carbon atoms, and R² is a straight chain alkylene group containing 1 to 5 carbon atoms.

30. The method according to claim 11, wherein the second antibody is a monoclonal antibody.

31. The method according to claim 25, wherein the derivatizing agent, is of the following structure:

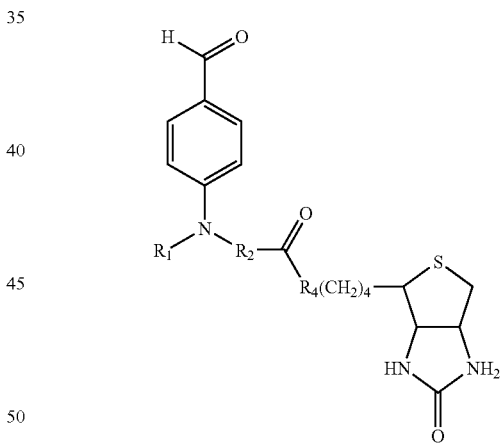

wherein R¹ is a straight-chain alkyl group containing 1 to 5 carbon atoms, R² is a straight-chain alkylene group containing 1 to 5 carbon atoms, and R⁴ is a straight-chain heteroalkylene group containing 2 to 10 carbon atoms and at least 2 heteroatoms.

32. The method according to claim 31, wherein R¹ is —CH₃, R² is —CH₂CH₂— and R⁴ is —NH(CH₂)₅NH— or —NH(CH₂)₂SS(CH₂)₂NHC(O)(CH₂)₅NH—.

33. The method according to claim 32, wherein R⁴ is —NH(CH₂)₅NH—.

* * * * *